United States Patent [19]

Fitzgerald

[11] Patent Number: 4,904,252

[45] Date of Patent: Feb. 27, 1990

[54] TOY DIAPER

[76] Inventor: Terry L. Fitzgerald, 15036 S. Alden, Olathe, Kans. 66062

[21] Appl. No.: 276,907

[22] Filed: Nov. 28, 1988

Related U.S. Application Data

[63] Continuation-in-part of Ser. No. 138,642, Dec. 28, 1987, abandoned.

[51] Int. Cl.$^4$ ............................................. A61F 13/16
[52] U.S. Cl. ................................................... 604/385.1
[58] Field of Search ................... 604/385.1, 385.2, 358, 604/395, 396, 387, 388, 389, 390, 391

[56] References Cited

U.S. PATENT DOCUMENTS

| | | |
|---|---|---|
| 3,141,461 | 7/1964 | Farris . |
| 3,359,980 | 12/1967 | Rosenblatt . |
| 3,800,796 | 4/1974 | Jacob . |
| 3,882,871 | 5/1975 | Taniguchi . |
| 4,259,957 | 4/1981 | Sonenstein et al. . |
| 4,402,690 | 9/1983 | Redfern . |
| 4,475,912 | 10/1984 | Coates . |
| 4,617,022 | 10/1986 | Pignuel et al. . |
| 4,681,581 | 7/1987 | Coates . |

Primary Examiner—John D. Yasko
Attorney, Agent, or Firm—Litman, McMahon & Brown

[57] ABSTRACT

A toy diaper for a child's doll and the like comprises primarily materials closely resembling those actually used in baby diapers, giving the toy diaper a realistic appearance on the child's toy. Tabs comprising a hook and loop type attachment material extend from the ends of the diaper for use in fastening the diaper on the child's doll.

6 Claims, 1 Drawing Sheet

TOY DIAPER

This is a continuation-in-part application of U.S. application Ser. No. 07/138,642 filed Dec. 28, 1987 and entitled TOY DIAPER, now abandoned.

BACKGROUND OF THE INVENTION

1. Field of the Invention

The present invention relates generally to toy diapers and in particular to toy diapers possessing realistic appearance and employing a hook and loop type fastener making the toy diaper reusable.

2. Description of the Prior Art

Realistic doll clothing, including toy diapers, is very popular among children. The baby doll diapers are comprised of materials possessing the appearance of disposable baby diapers which typically have a one-ply, non-absorbent outer layer and at least one bulky inner layer and possess adhesive attachment mechanisms.

The problem with many prior art baby doll diapers is that they fall short in creating a realistic impression in the minds of children and are not reusable.

A previous solution to this problem was to provide a scaled down version of a disposable diaper for use on toy dolls. However, these scaled down versions employ the same adhesive type fasteners as are used on actual disposable diapers. A problem with such toy diaper fasteners is that they can only be used once before the adhesive fasteners are substantially destroyed.

Another problem associated with scaled-down versions of disposable diapers is that they are often made with highly absorbent paper products which are costly and do not withstand the torturous environment of a toy. Further, because they are paper, they can not be readily washed without undergoing extensive damage to the paper components.

Heretofore, there has not been available a toy diaper with the advantages and features of the present invention.

SUMMARY OF THE INVENTION

In the practice of the present invention, a toy diaper is provided which is adapted for use on toy dolls. The toy diaper is comprised of layers of non-absorbent bulky materials which provide the feature of appearing to a child to be a real diaper when used on a doll. An attachment device in the form of a hook and loop fastener, such as is sold under the trademark Velcro, is connected to wings of the toy diaper for holding the wings in an overlapping position once the diaper is on the doll. The hook and loop fasteners also possess the feature that they may be connected and disconnected numerous times without wearing out. Because the materials used to create the realistic appearance are not highly absorbent paper products, the diaper toy may be washed repeatedly.

PRINCIPAL OBJECTS OF THE PRESENT INVENTION

The principal objects of the present invention are: to provide a toy diaper for use on a child's toy doll and the like; to provide such a toy diaper which appears realistic to a child; to provide a toy diaper with fastener mechanisms which may be operated numerous times; to provide a toy doll diaper with materials which can be washed repeatedly and which will withstand the torturous environment of a toy; and other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
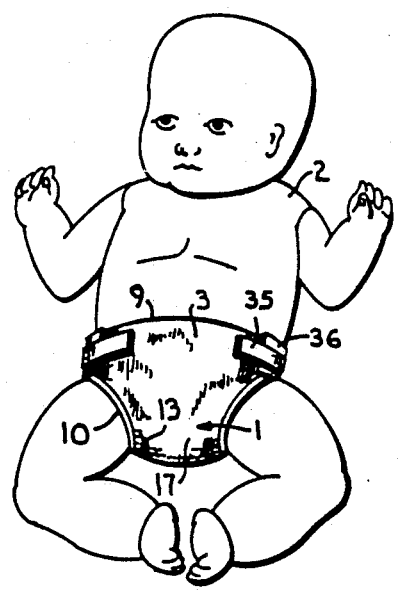
FIG. 1 is a front perspective view of a toy diaper embodying present invention, shown on a toy doll.
Figure 2:
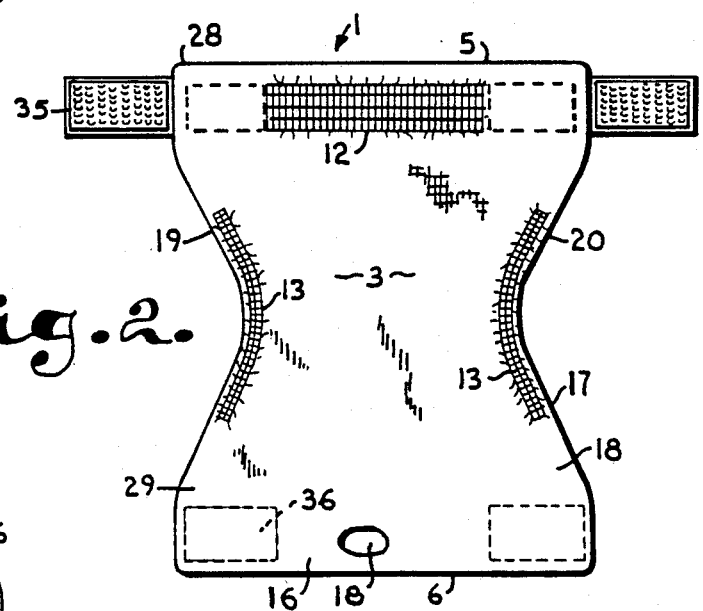
FIG. 2 is a plan view of the toy diaper.
Figure 3:
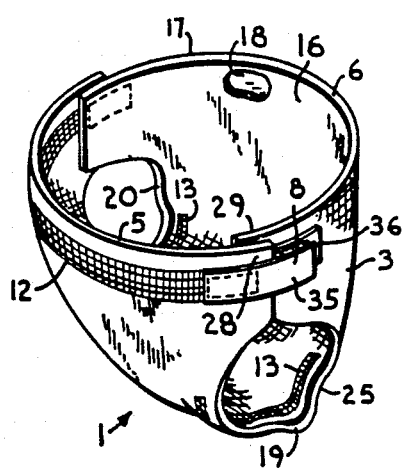
FIG. 3 is a side perspective view of the toy diaper.

The reference numeral 1 generally designates a toy diaper embodying the present invention. With reference to FIGS. 1, 2 and 3, the toy diaper 1 for a toy doll 2 has a main body 3, a first spaced end 5, a second spaced end 6, hook and loop fasteners 8, a first elastic gathers 12, a second elastic gathers 13, a first side 19 and a second side 20.

The main body 3 is comprised of an inner, single ply layer 16, an outer, single ply layer 17, and an intermediate, bulky layer 18. The intermediate, bulky layer 18 is fixedly attached to and sandwiched between the outer, single ply layer 17 and the inner, single ply layer 16. In the preferred embodiment the layers are stitched together. The outer, single ply layer 17 and the inner single ply layer 16 are chosen from materials which have an appearance similar to the outer, and inner non-absorbent layers of a standard disposable diaper.

The intermediate bulky layer 18 comprises non-absorbent polyester material. However, it is foreseen that other non-paper products which can withstand repeated washing may be used for the intermediate bulky layer 18. The intermediate, bulky layer 18, when fixedly attached to and sandwiched between the outer, single ply layer 17 and the inner, single ply layer 16, creates the bulky appearance characteristic of standard baby disposable diapers, the intermediate layers of which are composed of bulky, highly absorbent materials.

Leg openings 25 are defined by a first wing section 28 and a second wing section 29. The toy diaper is curved about an axis transverse to the first side 19 and the second side 20.

The first wing sections 28 are overlapped by the second wing sections 29 such that the first spaced end 5 and the second spaced end 6 align to form a complete loop to encircle a midsection 9 of the toy doll. Overlapping the first wing sections 28 and the second wing sections 29 causes the sides 19 and 20 to curve into a circle to form the leg openings 25. By adjusting the overlap of the wing sections 28 and 29, the diaper can be adjusted to accommodate dolls of various sizes. As the first wing sections 28 and the second wing sections 29 are adjusted, the second elastic gathers 13, which are sewn generally perpendicular to the longitudinal axis of a toy doll leg 10, are either stretched or allowed to contract to conform to the shape of the toy doll leg 10.

The first wing sections 28 and the second wing sections 29 are held in their overlapping positions on the doll by the hook and loop fasteners 8. Each fastener 8 has a hook section 35 and a loop section 36. The hook section 35 is attached to the outer side of the first end 5 at the end of a respective first wing section 28. The loop section 36 is attached to the outer side of the second end 6 at the end of a respective second wing section 29. When the first wing section 28 and the second wing section 29 are overlapped, the hook section 35 may contact the loop section 36 causing engagement of the hook and loop fastener 8. The hook section 35 is substantially longer than the loop section 36 to allow for adjustability of the toy diaper on the toy doll 2.

Because the hook and loop fasteners 8 are extremely durable, they may go through a multitude of engagement cycles prior to failure. Consequently, when the hook and loop fasteners 8 are fixedly attached to a toy diaper 1 having an outer, single ply layer 17, an inner, single ply layer 16, and an intermediate, bulky layer 18 comprised of durable, washable materials, the result is a toy diaper which is highly reusable.

It is to be understood that while certain forms of the present invention have been illustrated and described herein, it is not to be limited to the specific forms or arrangement of parts described and shown.

What is claimed and desired to be secured by Letters Patent is as follows:

1. A reusable toy diaper adapted for use on toy dolls with legs and a midsection, which comprises:
  (a) a main body; said main body is comprised of a layer of bulky non-absorbent material having the appearance of highly absorbent material used in disposable baby diapers and a layer of single ply material having the appearance of non-absorbent materials used in the outer layer of actual baby disposable diapers; and
  (b) hook and loop fastener means releasably connectable at the inner corners of the main body and comprising a hook section and a loop section for connecting two corners of the main body in overlapped disposition to form said toy diaper to the legs and midsection of the toy doll.

2. The invention as defined in claim 1 wherein an adjustment means is fixedly attached to the toy diaper allowing for use with dolls of various sizes.

3. The invention as defined in claim 2 wherein the adjustment means is comprised of elastic strips fixedly attached to a first or a second end to allow for variation in the sizes of the doll midsection.

4. The invention as defined in claim 3 wherein an adjustment means is fixedly attached to the main body adjacent to the leg openings to allow for variation in the size of the doll legs which is comprised of elastic stress material.

5. A reusable toy diaper adapted for use on toy dolls with legs and a midsection, which comprises:
  (a) a main body having inwardly and outwardly facing surfaces, a first end, a second end, a first side edge and a second side edge;
  (b) a first pair of oppositely directed wings extending laterally from said first end;
  (c) a second pair of oppositely directed wings extending laterally from said second end and adapted to overlap said first pair of wings to define doll leg and midsection openings;
  (d) hook and loop fastener means fixedly attached to said first and second pairs of wings and comprising a hook section and a loop section for maintaining said wings in overlapped disposition to form said diaper to the doll's midsection and legs; wherein said hook section is disposed on said outwardly facing surface of said first pair of wings and said loop section is disposed on said outwardly facing surface of said second pair of wings;
  (e) said main body being comprised of a layer of bulky material and a layer of single ply material;
  (f) said bulky material layer being the inner layer of said toy diaper for contacting the surface of the doll and comprising a non-absorbent material;
  (g) adjustment means comprised of elastic strips fixedly attached to a first or second end to allow for variation in the sizes of the doll midsection; and
  (h) adjustment means fixedly attached to the leg opening to allow for variation in the size of the doll legs.

6. A reusable toy diaper adapted for use on toy dolls with legs and a mid-section, which comprises:
  (a) a main body having inwardly and outwardly facing surfaces, a first end, a second end, a first side edge and a second side edge;
  (b) a first pair of oppositely directed wings extending laterally from said first end;
  (c) a second pair of oppositely directed wings extending laterally from said second end and adapted to overlap said first pair of wings to define doll leg and midsection openings;
  (d) hook and loop fastener means fixedly attached to said first and second pairs of wings and comprising a hook section and a loop section for maintaining said wings in overlapped disposition to form said diaper to the doll's midsection and legs; wherein said hook section is disposed on said outwardly facing surface of said first pair of wings and said loop section is disposed on said outwardly facing surface of said second pair of wings;
  (e) the main body comprised of an outer layer of single play material, an intermediate layer of bulky material, and an inner layer of single ply material;
  (f) said bulky material layer being that layer interior to the inner single ply layer and the outer single ply layer; said inner single ply layer for contacting the surface of the doll; said interior layer comprising a non-absorbent material;
  adjustment means comprised of elastic strips fixedly attached to a first or second end to allow for variation in the sizes of the doll midsection; and
  (h) adjustment means fixedly attached to the leg opening to allow for variation in the size of the doll legs.

* * * * *